United States Patent [19]

Gergely et al.

[11] Patent Number: 4,876,802
[45] Date of Patent: Oct. 31, 1989

[54] PROCESS AND MEANS FOR THE HEAT TREATMENT OF POWDERY OR GRANULATE MATERIAL

[76] Inventors: Gerhard Gergely; Irmgard Gergely; Thomas Gergely, all of A-1050 Vienna, Gartengasse 8, Austria

[21] Appl. No.: 877,112

[22] Filed: Jun. 23, 1986

Related U.S. Application Data

[63] Continuation-in-part of Ser. No. 766,884, Aug. 16, 1985, abandoned.

[30] Foreign Application Priority Data

Dec. 21, 1983 [AT] Austria ............................ 4465/83-1
Jun. 21, 1985 [CH] Switzerland ........................ 2640/85
Oct. 3, 1985 [CH] Switzerland ........................ 4267/85

[51] Int. Cl.$^4$ ................................................ F26B 5/04
[52] U.S. Cl. .......................................... 34/15; 34/33; 34/73; 34/92
[58] Field of Search ................... 34/15, 22, 33, 73, 92, 34/57 R, 57 E, 179, 181, 168

[56] References Cited

U.S. PATENT DOCUMENTS

| | | | |
|---|---|---|---|
| 1,614,253 | 1/1927 | Nielsen | 34/181 |
| 3,262,218 | 7/1966 | Cymbalisty | 34/124 |
| 3,874,092 | 4/1975 | Huttlin | 34/130 |
| 3,921,309 | 11/1975 | Nakayashiki | |
| 4,027,401 | 6/1977 | Fairbanks | 34/92 |
| 4,535,550 | 8/1985 | Walter | 34/135 |

FOREIGN PATENT DOCUMENTS

| | | |
|---|---|---|
| 12644 | 4/1969 | Australia . |
| 372299 | 9/1983 | Austria . |
| 0151782 | 12/1984 | European Pat. Off. . |
| 1060093 | 6/1959 | Fed. Rep. of Germany . |
| 2406347 | 8/1975 | Fed. Rep. of Germany . |
| 2224269 | 10/1974 | France . |
| 2422915 | 11/1979 | France . |
| 2031570 | 4/1980 | United Kingdom . |

Primary Examiner—Harry B. Tanner
Attorney, Agent, or Firm—Ostrolenk, Faber, Gerb & Soffen

[57] ABSTRACT

Solid, loose particulate materials are treated with vaporizable agent in a process chamber. The materials are combined with a mixture of hot gas and vapor in order to condense finely subdivided amounts of the treatment agent on the material. After a suitable time of reaction, the condensed material is partially removed from the treated material so that the pressure in the process chamber is reduced at least to the point at which the treatment agent partially evaporates, whereupon the portion which has revaporized is extracted from the process chamber. This cycle of introduction and removal of the treating agent is preferably repeated in a program-controlled operation until the desired result is achieved and a product which is suitably agglomerated is obtained. In the present process, particulate material in powder or granule form is agitated and heat-treated in a closed drum, by stirring agents and surface treated by a hot gas flow forced over or through the charge of the material and then extracted intermittently by a vacuum pump. The air is heated and vaporized so that the vapor does not condense on the charge material.

18 Claims, 3 Drawing Sheets

PROCESS AND MEANS FOR THE HEAT TREATMENT OF POWDERY OR GRANULATE MATERIAL

This application is a continuation-in part of Ser. No. 766,884 filed, Aug. 16, 1985 now abandoned.

BACKGROUND OF THE INVENTION

The invention relates to a process for the treatment of materials in a closed drum. This process is capable of effecting physical and/or chemical interaction between hot gases and/or a liquid treatment agent and the particles or components of the materials to be processed.

In the pharmaceutical industry there is a constant need to mix, heat, wet, and dry powders and granulates. Depending on the type and quantity of the raw materials, these treatment steps often require different procedures. Some raw materials may only be agitated and/or heated gently when wetted or dried, while others tend to form lumps and/or a coating that tends to prevent complete drying. The uniform distribution of solvents or wetting agents over relatively small amounts of auxiliary or active substances is also frequently difficult to achieve.

Diverse methods and devices have been proposed for the purpose of solving these problems, which in many cases are still unsatisfactory. Hence, the granulation of powders still requires multi-step treatment, while the drying of larger batches often necessitates lengthy treatments. This also applies for drying operations in which hot air is drawn through or over a charge of wet solid, loose material and/or where the moisture is to be removed by the application of vacuum. The latter operation especially has the tendency, where particles of the charge are heated at the surface and start to dry out, to form a coating which impedes or even prevents further drying. On the other hand, by the application of vacuum, the mixture cools down rapidly because the vaporizing solvent extracts evaporation heat from the material, such that the drying is slowed down despite the applied vacuum.

According to the state of the art, the process material is generally mixed with a liquid treatment agent which may then be removed by means of heating and/or pressure reduction. Especially in the case of relatively small treating fractions, the exact amount and uniform distribution of the treatment agent can be difficult to achieve. The treatment agent is also not always easy to remove, especially when the process material can only be separated with a high energy or process effort.

In the case of polar solvents, including water, acting as treatment agents, due to the high chemical and physical reaction capability of these agents, these problems are especially pronounced so that the boundaries between "chemical" and "physical" bonds or binding energies in systems with relatively large surfaces often becomes indistinct.

It therefore often becomes necessary to forego the use of treating agents which are cheap and free of ecological problems, and to substitute another agent, or to dilute an agent. It is increasingly important to find energy-saving and environmentally safe measures in the processing of fine-particulate substances in various fields of technology, ranging from the processing of foodstuffs and detergents through the processing of medicaments to fertilizer and building material technologies.

Until the present time, the theoretical aspects of treatment and processing of powders have still not been mastered but rather conventional methods were used. For example, in the manufacture of medicines starch is still being used as a binding agent, where a certain amount of starch with substantial amounts of water is hydrolyzed for every charge. The water must then be removed in long drying operations. The agglomeration or granulation of the mass, which is then reduced to the desired grain size, is thereby achieved. For this reason, little progress has been made in the automation of these methods.

If however, in a process broken down into steps, care is taken to supply sufficient heat and/or treatment agent in the desired concentration during these steps, possibilities for improvement can be found.

If it is desired to granulate a carbohydrate such as lactose or sugar with an active substance, the powder mixture is treated with water. Some parts dissolve and after drying, coarse-grained structures are obtained. However, complete uniformity in the composition and grain size is by no means assured.

A specific example for the special problems of treating solid, loose process material is in the agglomeration of powdery mixtures, with or without a reactive boundary surface area, such as in the manufacture or processing of preparations capable of reaction in the presence of water for the production of $CO_2$. Such materials are referred to below as "reactive products".

The manufacture of such reactive products is only one of many examples of the problems of treating fine-grained process material. Another example is the granulation of substances which are spray-dried or which are obtained by fine grinding, or by chemical surface reactions.

In the past, processes for drying having become known, e.g. according to EP-A-80,199, U.S. Pat. No. 4,535,550 or DE-A-29 42 325. They however have the disadvantage that for a prior coating, granulation or the like, it is not easy to distribute the coating or granulation material uniformly in the charge material.

It has also already been proposed to supply a vacuum to the agent into the drum to achieve the desired treatment before drying is resumed, such as taught by DE-C-1,060.093, DE-A-22 18 729 or AAT-C-372.299, or to jet the agent into the drum, according to EP-A-80,199. However, in this case the treatment agent concentrates at the point of initial contact with the particles and forms initial large clumps, it being difficult or in some cases impossible to subsequently distribute the treatment agent uniformly in the charge material.

In general, during the treatment according to the present invention, such as during granulation of an effervescent mixture, heated air is laden with water vapor which condenses on the product. Afterwards the vapor is shut off, with carbon dioxide formed, as well as water vapor being removed by hot air. Vacuum is maintained at between 600–900 mbar.

In EP-A-151 782, the one-time treatment of a solid, loose material in a vacuum drum with hot air flow, eventually laden with water vapor, is disclosed with the hot air flow being conducted through the charge. However, several disadvantages are evident. In the mixture, the nozzles can clog with moist, fine-grained material therein.

To achieve the treatment in one operation, the temperature and/or concentration of the vapor must be relatively high. However, that results in local overheating and/or a non-uniform condensation.

To a certain extent disadvantageous, is the one step process described in DE-B-1,060.093, in which heating is not necessarily done, but for the purpose of granulation of a powder, a vaporous solvent is taken in a single time and then removed after condensation by vacuum.

In GB-A-2,301,570, a drying process was described in which liquid or pasty products are subjected intermittently to a vacuum and then to a heated, dry gas flow. However, in this process even with products containing relatively little moisture such as yeast or onions, long drying times are required. This is associated with the fact that the air flow is conducted in a circuit and is freed of solvent vapor via an absorber bed, involving a considerable pressure drop. Therefore, the intake phase takes too long while the air flow brings along little heat to apply to the material which has been cooled down too much by the applied vacuum. To overcome this problem, a heat exchanger is used for preheating the air although even this has a certain resistance to flow. If this resistance is now overcome in the conventional manner, a relatively high vacuum will occur in the drum, resulting in severe cooling of the material. By virtue of hot air being applied by vacuum, there is a reduction in temperature of the particles caused by the evaporation of the moisture to be removed.

The usual treatment operations between a powdery particulate material and a liquid, such as a solvent, are broken down into individual steps which are easier to monitor, control and programmable. Up to this time, this did not appear possible in connection with such treatment operations because liquids such as binding agent solutions, or even water, are still too viscous to enable uniform distribution to be achieved in particle sizes between 10 and 100 microns. To date, a surplus of solvent had to be added to the solvent to achieve wetting of all particles.

SUMMARY OF THE INVENTION

If in accordance with the present invention, binding agents, fillers and active substances, in powder form, are mixed and then treated stepwise with small amounts of water to the effect that the viscosity of the solvent, which may be water, is drastically reduced by being present in the vapor phase, and diluted by hot air, the problems of the prior art are solved.

Water vapor alone will not, in all cases, produce usable results because water vapor will condense at the place of its entrance on a cooler surface, hence quickly on the particles to be granulated, and thereby lead to the formation of clogs. For example, if 10 liters of air at 120° C. contain only 100 ml water, then condensation proceeds considerably slower because the condensation process, which for the vapor is endothermic, first extracts heat from the air, thereby cooling it down before the water enters the liquid phase.

The parameters required for reproducible and programmable procedures are therefore, the temperature of the process material and the infed air, the proportion of the vaporous reaction partner or of the treatment agent in the dilution phase and the selected vacuum In this way the wetting of the process material particles can be split up into several steps. Also the increase in grain size can be controlled precisely and monitored so that the process can be interrupted at the appropriate time.

For example, by the treatment of a mixture of 80 parts of lactose, 15 parts of a pharmaceutically active substance and 5 parts of binding agent, about 10 times in succession, each time with only 3 parts water in about 15 parts inflowing hot air, and by drying the mixture after each treatment by the application of vacuum, the desired control of the process is achieved. For each of the programmed operating modes, only three control means in the configuration described later need be provided, namely the inflow valve for the preadjusted water vapor-air mixture, the valve to the vacuum pump for changing from a low constant vacuum for the condensation to a full vacuum for drying, and finally the control to regulate the agitation rate during condensation and drying.

The hot air, which is forced into the drum is eventually laden with water vapor with a much higher specific heat content than the air, will give its heat off to the material, resulting in the desired treatment effect, that is, the evaporation of the moisture on the respective grain surface. Since previously vacuum prevailed in the charge, the hot air penetrates into all parts of the charge.

This hot air inflow is important and is superior to conventional vacuum treatment of material.

For a simple drying process, the vapor content of the air must be optimized. More vapor does give off more heat to the material, but for reasons of equilibrium, it prevents more moisture from vaporizing. However, for a person skilled in the art this is a parameter which can be determined in terms of the material to be treated.

In the next phase in which vacuum is applied, this moisture is extracted. Due to the fact that the vacuum phase usually comprises only a fraction of the hot air pressure phase, only a minimum amount of heat is lost. The heat loss can be reduced even further by interrupting the supply of hot air during at least a part of the extraction phase.

If in this phase a coating should form on the grain surface, then during the succeeding hot air pressure phases, the moisture inside the grain again has the opportunity to diffuse ("migrate") to the outside, and thereby to dissolve the coating which has formed and to evaporate into the hot air.

The temperature of the hot air and the cycle times can be varied depending on the product to be treated. With the process according to the present invention, it is also possible to dry charges of fine powder, such as milk sugar, powdered sugar, paracetamol, naproxen etc. in quantities of 100 or more kg that contain e.g. 10 to 20% moisture within a time of 30 to 60 minutes, and often in only 20 minutes. The cycle time can be controlled and the process can be terminated by continuous moisture measurement. It is also necessary to control the difference in pressure between the hot air inflow and the extraction in the vacuum phase.

In many cases it is desirable to periodically agitate the charge by rotation of the drum and/or by means of a stirring apparatus. However, excessive agitation should be avoided because it will destroy granulate which has formed or is in the process of forming, and because undesirable dust can be churned up.

The invention consequently provides an intensified supply of heat energy to the product being treated, and the better distribution of a treatment agent, e.g. of a solvent, in the product being treated.

Namely, if the gas treatment agent is introduced without carrier gas and only at one location, it may react with the particles of the material being treated that it first contacts. In this case, uniform treatment becomes very difficult. Even the application of vacuum that in any case has a homogenizing effect on the treatment process, does not suffice to make the treatment controllable and reproducible.

In most cases, the gas flow will consist of air, but for certain applications, such as when oxygen is to be excluded, nitrogen, argon or carbon dioxide can be used.

In principle, an embodiment of the invention is based on the forcing of heated air through the product by means of a slight vacuum to a vessel which is fitted to the entry of a heat exchanger which heats the air. The vessel allows solvent to drip or be entrained in the air flow under equal inflow pressure conditions. Here, the temperature of the heat applied must be somewhat higher than the boiling point of the corresponding solvent. The solvent goes to the heat exchanger where it evaporates and passes together with the hot air into the flow inlet of the vacuum agitator drum. It is possible to arrange the flow inlet at such a location that the flow passes through as large a bulk height of the powder mixture as possible. This is accomplished with a vacuum drum which can be adjusted such that at an inclination of about 30°, the air-steam mixture entry is at the lower point of the powder mass contained in the drum. The gas mixture is preferably fed in through the perforated stirrer which will be described below, yielding an especially uniform distribution of the solvent vapor over the entire powder mixture.

Concurrently with the powder mixture being agitated, the hot air together with the solvent vapor is now cooled down on the powder or particle mass, and the solvent vapor condenses on the particle surface. The vaporization heat thereby given off is transferred to the product and increases the product temperature. In this way, it is possible easily, with low solvent consumption, to soften parts of the powder mixture - especially on the surface of the powder particles - for granulation purposes, or also to dissolve binders present in the powder mixture, rendering a supply of solutions unnecessary.

The amount of heat supplied by the condensation energy is then usually adequate to again vaporize the solvent when the vacuum is applied. In this way, the process can be continuously carried out by the application of a certain vacuum so that a certain amount of solvent condenses in the powder mass, and when a certain temperature is reached, the inflowing solvent revaporizes and is condensed in the downstream condenser. Continuous granulation processes can thereby be realized.

This process is also suitable for removing water of crystallization out of substances. For example, lactose can be partially dehydrated or ampicillin can be freed of water of crystallization by being treated with hot saturated isopropanol-steam, accompanied by hot air.

A further deficiency especially occurring in the case of vacuum drums is the poor transfer of heat from the heated drum wall or from the hot gas that has a low heat content to the product to be treated. In this way, it is even possible to clean the wall during agitation by inflowing or imploding liquids.

The process according to the present invention may be used for granulation, especially if it is operated in a vacuum, and using stirring elements moving the product in the drum against the force of gravity.

It is another object of the present invention to devise a process and a system by which it is possible in a relatively short time, to treat and eventually dry or granulate very uniformly, a charge of powder even in the event of the material consisting of sensitive substances.

The process described above enables the treatment steps to be controlled precisely and provides uniform treatment, or distribution of treatment agents, even if the amount of treatment agent in relation to that of the process material is very small, or if there is a tendency toward undesired or strong interaction between treatment agent and process material or if under normal conditions, the removal of the treatment agent involves application of high energy.

To perform the process according to the present invention, particulate process material, with grain sizes of for example 0.01 to 1.5 mm, can be introduced into the process chamber i.e., a vacuum chamber with mechanical and/or pneumatic equipment to agitate the process material, for the purpose of premixing the components, or in the form of the individual components.

Suitable agitation apparatus exerts, at most, low shear forces on the material such that they agitate the material in the direction opposing that of gravity, especially two or three-dimensionally oscillating mixing apparatus. Also preferred are mixing apparatus which effect mechanical agitation, as well as pneumatic agitation of the process material, such as hollow mixing arms, through openings in which hot gas can be blown in.

In this application, the term "hot gas" signifies a relatively ideal gas or gas mixture, i.e. in comparison with the treatment agent vapor, such as nitrogen, air, noble gas or carbon dioxide, insofar as undesired reactions are not thereby caused.

With the process according to the present invention, the temperature of the hot gas must be higher than the vaporization or boiling temperature of the treatment agent at the normal pressure of about 1 bar, typically at least 10° C. higher and preferably at least 20° C. higher. The upper limit for the temperature of the hot gas is not especially critical, but for reasons of thermal sensitivity of the process material, as well as unnecessary thermal stress of the equipment used, and for reasons of minimizing the energy consumption, said temperature is not normally increased above the stated minimum values.

At normal pressure, treatment agents that are suitable for the process according to the present invention must evaporate (or sublimate) in hot gas at least almost entirely free of residues, and they must be condensable at normal pressure and temperatures of typically between zero and 200° C., and preferably between room temperature and 100° C.

At normal temperature, liquid and especially polar treatment agents are usually preferred for the process according to the present invention. Water is especially preferred, but organic solvents are not excluded. A treatment agent suitable for the process according to the present invention must be capable of condensing on the warm process material in the form of fine particles, and of being easily removed from the heated material by reduction of pressure prevailing in the process chamber.

When water is used as the treatment agent, and the hot gas such as air has a temperature greater than 100° C., preferably at least 110°-150° C., the condensation on the typically 50° C. warm process material takes place at about 200-800 mbar and evaporation is at nearly the same process material temperature and 10-30 mbar pressure in the process chamber.

To a major extent, the concentration of the treatment agent vapor in the hot gas can be varied for example from 0.1 to 50% vol. or more. The use of mixtures with higher treatment agent vapor fractions is possible, but usually not preferred. Typical hot air/water vapor mixtures contain a per unit volume of 1 to 5, and preferably 2 to 4 units. Before and/or after, the treatment of the process material with the treatment agent or hot gas or, if desired, cold carrier gas, can be passed through the process material to achieve a desired heating or cooling effect.

For the purpose of producing a mixture of hot gas and treatment agent vapor (referred to below as gas/-water vapor mixture), the treatment agent can be fed into the heat exchanger, which also serves the purpose of heating the gas.

Before introduction of the gas/water vapor mixture, the material fed into the process chamber is preferably preheated to a temperature that is about 30° C. to 60° C. below the normal boiling temperature of the treatment agent at normal pressure.

This preheating of the process material can be done with hot gas and/or by heating the external wall of the process chamber. The heat can be transferred from the chamber wall to the process material directly, i.e. by the contact of the process material with the heated wall, or insofar as substantially reduced gas pressure does not prevail, directly, via the gas/water vapor mixture located in the chamber.

To achieve condensation of the treatment agent vapor on the process material that is primarily on the surface of the solid particles of which the process material is formed, in as uniform and finely distributed manner as possible, at normal or weakly reduced pressure, the gas/water vapor mixture is generally applied to the preferably agitated and heated material such that a coherent liquid phase does not form between or on the process material particles. For many applications, the process is conducted such that the process material particles do not become "wet" in the sense that a coherent liquid film is formed on each particle, or that the space between the particles is filled at least almost entirely with liquid.

For an optimum distribution of the treatment agent on or in the process material particles, it is preferred that the treatment agent be condensed on the process material particles in the form of fine, normally suspended droplets ("mist"), and absorbed by or reacting with the surface of the process material about just as quickly as it condenses thereupon. The selection of the pressure, temperature and concentration for the adaptation to a given process material can be optimized by one skilled in the art.

The "condensation phase" step can be terminated with the introduction of the gas/water vapor mixture, or extended beyond this point for the purpose of distribution of the condensate in the material and/or to enable the interaction between material components. This phase, consisting of the condensation itself and the eventually succeeding treatment agent action, takes typically a few seconds to a few minutes, e.g. 10 sec. to 10 min., rarely longer.

The "condensation phase" is terminated by reducing the pressure in the process chamber until, at the prevailing temperature of the process material and the reduced pressure, the boiling point of the treatment agent is at least reached and preferably exceeded.

With this pressure reduction of 10 to 50 mbar, the treatment agent removal phase that can effect partial and typically at least 50% or almost complete removal of the treatment agent, will start. This phase can also be completed typically in a few seconds to a few minutes, such as 30 sec. to 30 min.

A single condensation phase, followed by a removal phase, is referred to here as a "treatment cycle". As mentioned above, according to the present invention the treatment is performed in more than only one cycle, preferably in five or more cycles, until a specific end condition, e.g. a desired degree of agglomeration and-/or reaction and/or diffusion of the process material, has been achieved.

The procedure is repeated in cycles so that the free space in the reaction drum is not filled with carbon dioxide and water, but so that they are removed—eventually—during the inflow of the hot air/vapor-mixture. The advantage is that the product remains at the given temperature because the exothermic procedure is compensated for by vaporous hot air. When the mist is finely divided, the reaction is not so vigorous but can easily be carried out several times.

Reactive products according to the present invention comprise e.g. a normally solid, crystalline organic acid such as citric acid, tartaric acid, malic acid, fumaric acid, adipic acid, ascorbic acid or mixtures of such acids with finely divided reaction partners, such as the carbonates or bicarbonates of alkali or alkaline earth metals, oxides or hydroxides of earth alkaline metals, zinc or iron or other salts of acids weaker than the carbonic acid used, such as zincglycerophosphate, iron-gluconate, calcium-lactate, etc.

This results in an optimized boundary surface between the acid and carbonate particles in that almost every acid particle is enveloped by carbonate particles. Agglomerate can naturally also contain several acid particles, of which however each one is almost completely enveloped by carbonate particles as will be described below.

Here, additional binding agents and extenders, such as sugar, mannite, starch or lactose can be used. A compound of the acid and the carbonate, e.g. calcium citrate which accounts for about 1 to 5% of the weight of the constituent components, said compound being formed by in-situ incipient reaction, preferably serves as a binding agent between the acid and carbonate particles.

Moreover, by means of a corresponding repetition of cycles with the process according to the present invention, additional components, e.g. coloring or active substances that have a solubility of typically at least 5 g/liter in water at process material temperature, can be distributed uniformly in a particulate process material.

In this way it is especially possible to manufacture a new reactive product for effervescent preparations or tablets with difficult soluble carbonates such as magnesium or calcium carbonates, or oxides such as magnesium oxides as well as toxicologically acceptable fluoro compounds such as disodium fluorophosphate, in a distribution as uniform as needed for such products. The carbonate or oxide particles are fixed in an especially simple and cost-saving manner on the surface of the acid particles or are imbedded therein An especially intimate contact between the difficultly soluble reaction partners with the crystalline acid particles is of importance and is improved by the addition of pulverized acid. For reaction compounds other than alkaline earth carbonates, it is advantageous to afterwards fix easier soluble alkaline carbonates in order to manufacture effervescent mixtures.

It is surprising that a reactive product, with calcium carbonate as a $CO_2$-forming agent with a content of water-soluble fluorine compounds, e.g. in fractions of 0.05 to 10% of the weight, is obtainable and usable. It would rather be expected that in the manufacturing process, the soluble fluorine compound would be converted quantitatively with the calcium carbonate or calcium citrate into insoluble calcium fluoride, and it is not excluded that precise controllability of the process according to the present invention, preferably used to manufacture such reactive products containing fluorine will play an important role.

Even the above mentioned difficult soluble oxides, such as magnesium oxide, magnesium oxycarbonate, iron oxide, zinc oxide, etc. and others can be attached at the surface of an acid by the instant process because they react partially with the organic acids when they are wetted by the condensing mist and after drying adhere to the surface.

Thereby, when wetting the organic acid with the oxides attached to its surface, be it in the form of an instant product or as a reactive effervescent product, the procedure of the reaction to magnesium citrate, iron citrate, zinc citrate, etc. initiated by the water vapor during manufacture is completed.

A configuration especially suitable for conducting the process according to the present invention and the structure of certain reactive products are explained in greater detail on the basis of the attached drawings.

BRIEF DESCRIPTION OF THE DRAWINGS

The invention is described in detail in the attached drawing, and in the following examples. However, the data given are by no means to be construed as constituting a limitation. In the drawings.

DETAILED DESCRIPTION OF THE INVENTION

Figure 1:
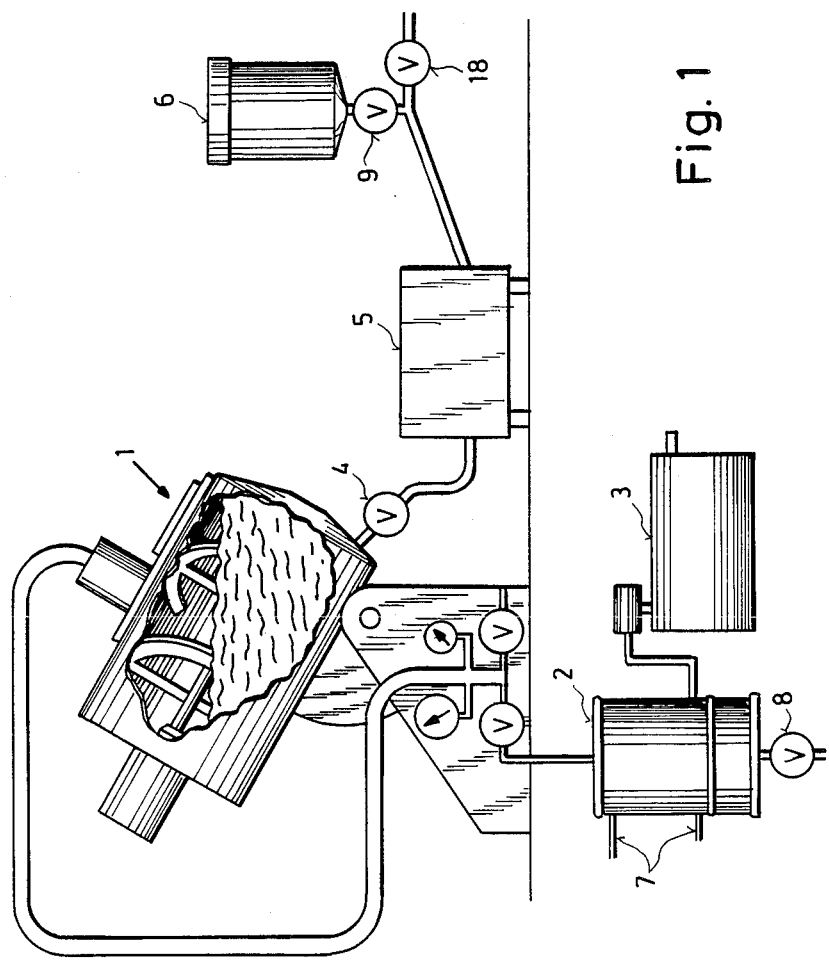
FIG. 1 is a schematic arrangement of a system for realizing a first embodiment of the process according to the present invention.

A vacuum mixer 1 is connected via solvent condenser 2 to vacuum pump 3. The condenser 2 is furnished with a cooling water inlet and outlet 7 and a condensate drain 8. The inclined vacuum drum 1 is, via gas or steam inlet valve 4, connected with heat exchanger 5 in which air supplied by a compressor via the inlet valve 18 is heated. A treatment agent is added in the form of vapor from the solvent feed device 6 through value 9. The workings of this system are described in Examples 1 to 13.

Figure 2:
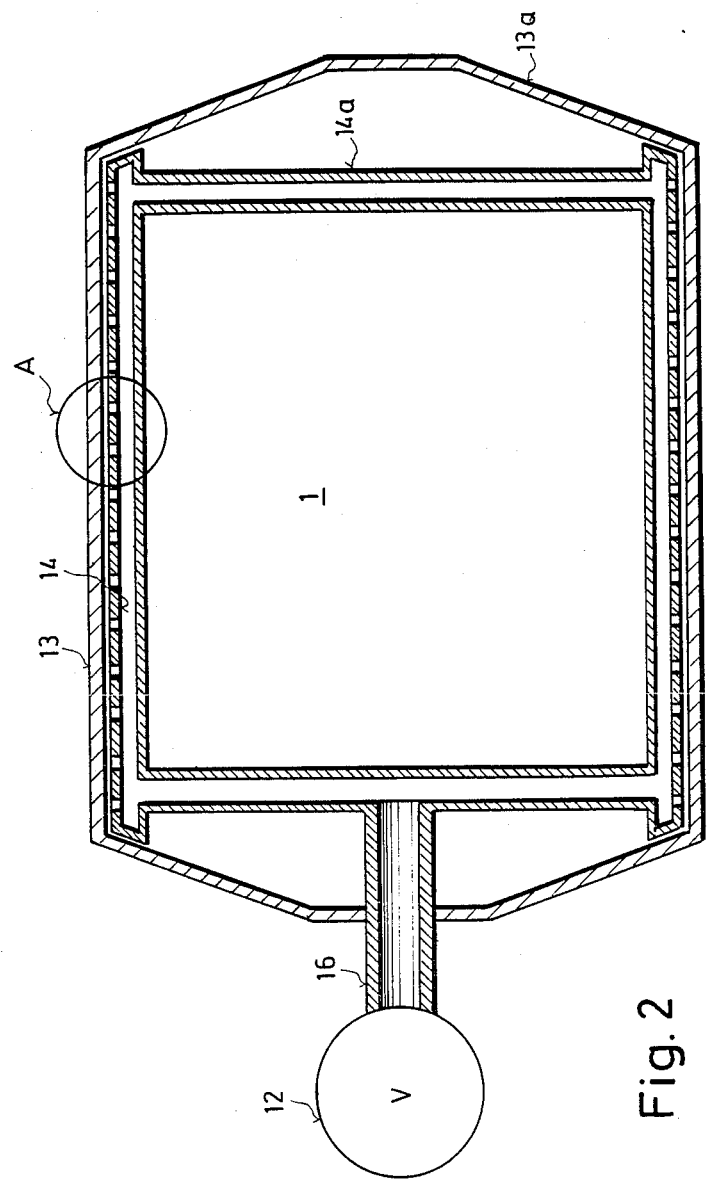
FIG. 2 is a schematic cross-sectional view of a vacuum agitator and treatment drum for realizing a second embodiment of the process according to the present invention.

According to a second embodiment of the invention, a stirrer 14, 14a (FIG. 2) is located in the hollow vacuum drum 1. The drum 1 has a wall 13 which can possibly be heated. A sealed hollow shaft 16 extends into the drum and is connected to stirrer 14 which comprises hollow bar elements. A valve 12 is installed upstream of the hollow shaft 16. Discharge openings are provided in parts of the hollow stirrer 14 opposite drum wall 13 in the form of holes or slots facing the drum wall, through which the treatment medium supplied through the hollow shaft 16 is fed into the drum.

It is apparent that discharge openings can also be provided in part 14a of the stirrer opposite the truncated cone head 13a of the drum, and that this part of the stirrer can be matched to the contour of the head 13a, so that at this point the same effect as with the cylindrical side walls is also achieved. Similarly, it is possible to provide discharge openings on the hollow shaft and on the sides of the stirring elements facing the interior of the drum.

It is also conceivable to use the hollow stirrer according to the present invention in a cylindrical drum 1, the drum being constructed as a fluidized bed dryer with dry air being fed into the drying drum through the discharge holes of the stirring elements instead of through the normal netting.

Figure 3:
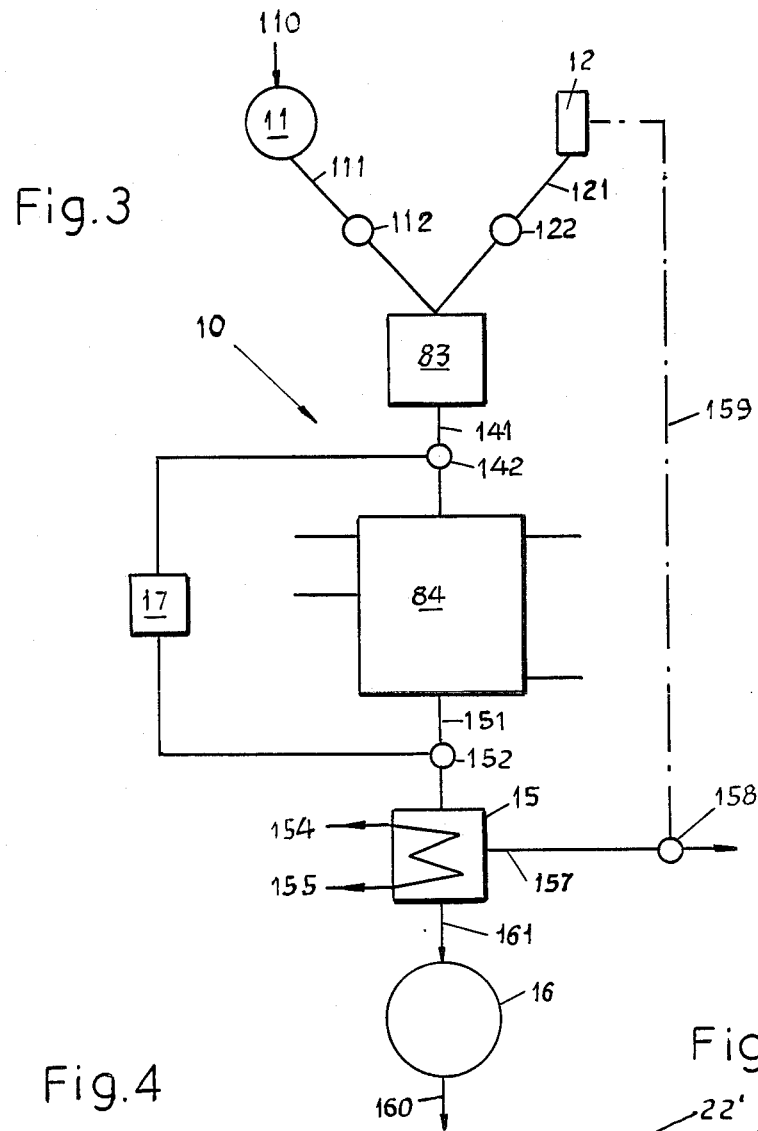
FIG. 3 shows the diagram of a configuration for conducting the process according to the invention.

FIG. 3 shows in detail the schematically illustrated configuration 10, encompassing a pump or a compressor 11 that draws in a gas, e.g. air at 110 and delivers it through the pipe 111 with optional valve 112 into the heat exchanger 83. The pump 11 has a delivery capacity of e.g. 10 to 100 liters/minute. The pressure of the gas when leaving the heat exchanger is adjusted to achieve the desired parameters of the process, e.g. to 1.5 bar.

The tank 12 contains the treatment agent for dispensing it via pipe 121 at an adjusted rate with the valve 122 into the heat exchanger 83 where it is, if desired, vaporized to produce a mixture of the gas and treatment agent vapor.

The heat exchanger is connected via pipe 141 and control valve 142 with the process chamber 84, into which the process material or the process material components G can be fed, and from which the finished product P can be drawn.

The process chamber 84 is supplied with heat W, e.g. by means of a heating jacket (not shown) and with agitation energy E, e.g. by means of a mechanically and/or pneumatically acting stirring apparatus (not shown) for agitating the process material. The process chamber 84 is also connected via pipe 151, control valve 152, and optional condenser 15 and pipe 161 to a suction or vacuum pump 16 which discharges the gas extracted from the treatment chamber 14 and possibly the treatment agent not removed in the condenser 15 through pipe 160, possibly via a cleaning system, to the atmosphere, or recirculates them to the heat exchanger 83 (not shown). The capacity of the pump 16 is preferably at least as high as that of pump 11.

The optional, and not preferred condenser 15, in the case of water being used as the treatment agent, can be kept in operation via coolant lines 154, 155, the condensed treatment agent being removed from the treatment agent tank via pipe 157 or eventually supplied thereto via valve 158 and return line 159.

To carry out a preferred embodiment of the process according to the present invention, the configuration 10 has a program control 17 which in the simplest case, controls only the opening/closing of the valves 142, 152, as well as valve operation timing.

If all parts of the configuration 10 are in service, the condensation phase can be initiated by opening valve 142, with valve 152 completely or partially closed, and terminated, i.e. the removal phase initiated, by closing valve 142 and opening valve 152.

Figure 4:
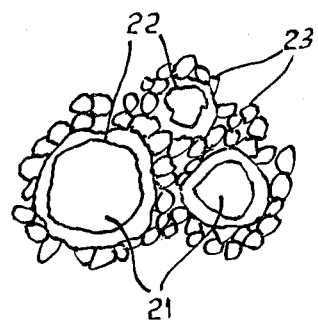
FIGS. 4 and 5 are diagrammatic cross-sectional representations of agglomerates obtained in accordance with the present invention.

FIG. 4 shows a schematic cross-section of a stereospecific agglomerate which has a multitude of cores 21.

The cores represent e.g. the relatively coarse-grained acid particles of a reactive product, which as $CO_2$ forming agent, contains a relatively fine-particulate calcium carbonate, represented by particles 23. At least 80% of the surface of every core 21 is covered by the particles 23.

Shown between the cores 21 and the carbonate particles 23 are the structurally simplified and proportionally exaggerated binding agent layers 22 as can be produced in situ in a reproducible manner with the process according to the present invention by incipient reaction of the acid with the calcium carbonate in the presence of small amounts of water, typically in fractions of 1 to 5% of the weight of the acid and the carbonate particles.

The cores 21 are normally not spherical, but generally granular, as is typical for more or less crystalline substances.

The cores can also be of different size, as long as they are relatively coarse in relation to the carbonate particles.

Figure 5:
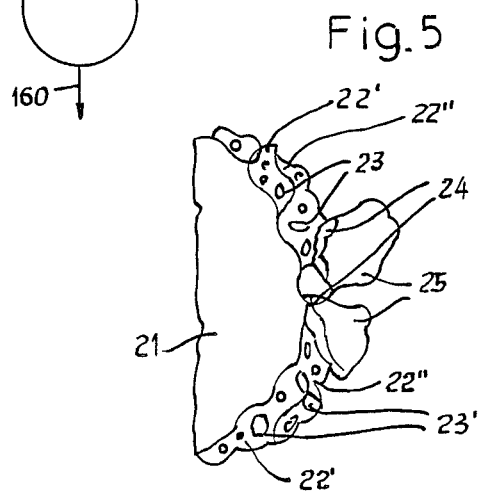

FIG. 5 shows an enlarged part of a citric acid crystal 21' that has been treated according to the invention, magnesium oxide and potassium carbonate. In a first cycle, a layer 22' comprising powdered magnesium oxide and citric acid has been applied, whereby the magnesium oxide particles 23' are surrounded by a layer of magnesium citrate (not shown). In a second cycle, a layer 22" consisting of the same particles was applied. In a third cycle potassium carbonate crystals 25 were applied, whereby in the zone of contact of layer 24, potassium citrate was formed. It is well understood that the border lines shown between the single particles and layers do not exist as such but are at least partially effaced by diffusion.

In a similar way, a reactive product according to the invention may be designed such that the particles 23' are or contain a toxicologically acceptable, watersoluble fluoro compound or other finedly-grained reaction partners.

The invention will now be explained in greater detail, but should not be limited to, the following examples.

EXAMPLE 1

(granulation of powdered sugar):

Water totaling 4 to 5 liters in the solvent feed device (6) are required for a drum capacity of 200 kg powdered sugar.

When the powdered sugar has reached a product temperature of 60° C. and the heat exchanger is at 120° C., air is introduced under a pressure of 0.2 to 0.5 bar at the compressor. The inlet valve (4) is then opened and the vacuum pump is adjusted such that the vacuum applied to the drum is about 800 mbar.

At this point, the valve (9) is opened and the water quantity for granulating over a period of 10 to 20 minutes is allowed to flow into the system. The water vapor produced at (5) flows via valve (4) through the powdered sugar in the vacuum mixing drum (1). The powdered sugar is mixed at a speed of about 20 rpm.

At first, the water will condense, but when the temperature of the powdered sugar increases to 70°-75° C. due to condensation heat, it will revaporize and condense in the condenser (2). The granulation progress is observed in the vacuum dryer. When granulate formation is adequate, the valve (4) is closed and the vacuum pump adjusted to full vacuum capacity, whereby the water remaining in the granulate particles is removed and a dry granulate produced.

EXAMPLE 2

Lactose weighing 200 kg and 6 kg of polyvinyl pyrrolidone of medium chain length are placed into a vacuum mixing drum and mixed. In the vacuum mixer, the product mixture is heated up to 50°-55° C. with a jacket temperature of 70° C.

The solvent feed device (6) contains 15 liters of alcohol. As under Example 1, in this case the heat exchanger temperature is increased up to 120° C., the compressor pressure is again brought up to 0.2 to 0.5 bar, but the vacuum is set to 600 mbar. Under these conditions at an agitation intensity of 20-30 rpm, 15 liters of alcohol—mixed via the heat exchanger (5) as a vapor with hot air—are allowed to flow within about 10 to 15 minutes through the lactose/PVP mixture. Since alcohol condenses somewhat differently than water, this influx is especially effected through the perforated stirrer. The influx at the bottom of the vacuum mixer through the bulk height at the same time must be increased to about 20 minutes, since the influx must proceed slowly. When the desired granulate size is reached, the line is closed at (4) and drying is done by the application of full vacuum.

EXAMPLE 3

(partial drainage of lactose):

Lactose weighing 200 kg containing water of crystallization are heated to 80° C., and 20 liters of isopropanol are introduced via the solvent feed device.

At a heat exchanger temperature of 90° C. and a vacuum of about 300 mbar, hot air is drawn by the compressor at 0.2 to 0.5 bar through the system. By opening the valve (9), isopropanol is allowed to pass through the lactose in a time of about 15 to 20 minutes, while a part of the isopropanol recondenses. By the vaporization heat given off the product, the temperature increases, so that subsequently isopropanol reevaporates and is condensed in (2).

After the process is completed, drying is again done by the application of vacuum, whereby a product is obtained consisting of approximately 30% anhydrous lactose. This mixture of anhydrous and hydrous lactose can be pressed directly into tablets, and corresponds to the known, directly pressable mixtures of alpha and beta lactose.

EXAMPLE 4

(dehydration of ampicillin)

With a jacket temperature of 40° C., an applied vacuum of 800 mbars and a compressor pressure of 0.2 to 0.5 mbar hot air of 130° C. at the heat exchanger (5) is allowed to pass through 200 kg of ampicillin. The solvent feed device (6) contains 60 liters of isopropanol, which vaporizes at a rate of 20 liters per hour through the heat exchanger and is drawn through the isopropanol containing water of crystallization—condensing only partially. After vaporization of the entire isopropanol and final drying by application of full vacuum, the water content of the ampicillin has dropped from about 13.4% to 0.4%.

EXAMPLE 5

(starch granulation)

Lactose weighing 160 kg and 20 kg starch are placed in the vacuum drum. At a jacket temperature of 100° C., the mixture is heated to 80° C.

A suspension of 20 kg of starch in 20 liters of water is prepared and the suspension is drawn in by means of a three-way valve at valve (4).

After mixing at 30 rpm, 10 liters of water are drawn via the solvent feed device (6), the heat exchanger temperature being 120° C., the compressor pressure is 0.2 to 0.5 bar, the vacuum in the drum is about 700 mbar and the influx period approximately 10 minutes.

By application of full vacuum, a dry, extremely uniform granulate of starch/lactose is produced.

This process is not optimally suited for the perforated stirrer because during formation of the starch paste, the holes in the stirrer could be clogged. This process is advantageously performed by drawing in at the bottom of the vessel.

EXAMPLE 6

5 parts of starch are mixed with 10 parts of lactose and heated to 80° C. by the application of a shell temperature of 100° C. The 15 parts of water are introduced and distributed by brief agitation. After reaching a temperature of 80° C., the starch is hydrolyzed by intermittent agitation.

Then, 80 parts of lactose and 15 parts of starch are added and the entire mass is mixed, whereby the hydrolyzed starch is distributed through the entire product. Then preheated hot air at a temperature of 100° to 150° C. is allowed to flow through the product via the perforated stirrer or via a nozzle, such that the vacuum in the drum reaches 0.2 to 0.3 bar.

A very regular granulate is thereby obtained which, after the addition of talcum and magnesium stearate, makes regular, very quickly decomposing tablets.

After the solution of the binder has been distributed in lactose, the active ingredients can preferably be added together with starch, and in this condition they combine uniformly with the granulates.

EXAMPLE 7

This example describes the production of a reactive product suitable for effervescent preparations.

Citric acid totaling 43 kg with grain sizes of between 0.4 and 0.6 mm are mixed with 22 kg citric acid of grain size 0.1 mm and heated in a vacuum mixing drum at process chamber 84 with a shell temperature of 65° C. to 45° C. Micronized calcium carbonate totaling 20 kg is then introduced. After evacuation to remove any residual moisture, the material is heated back up to 45° C.

At this point a constant vacuum of 600–900 mbar is generated in the vacuum mixing drum, and the heat exchanger 83 for heating the air to 120° C. gas outlet temperature is activated.

The pumps 11, 16 and valves 142, 152 are adjusted such that at 700 mbar, about 600 to 800 liters of hot air can flow into the process chamber 84 per minute. A quantity of 500 ml of water is now allowed to flow within 2 minutes out of the tank 82 into the heat exchanger, in which process a ratio of 1 volumetric part water vapor to 2 to 3 volumertic parts of hot air will ensue. Since at 900 mbar the boiling pressure of water is approx. 96° C., the water vapor condenses on the process material which has a temperature of about 45° C.

While being mixed three-dimensionally during the intake, the water vapor material condenses in the process in the form of very fine droplets. At the same time the production of $CO_2$, which is extracted via the vacuum pump 16, starts.

After the aforementioned quantity of water is introduced, the reaction is allowed to run for one minute, and then full vacuum is applied. With an adequately dimensioned vacuum pump (100–200 m³ per hour), at about 20 mbar, the water can be removed within 2–5 minutes.

The following heat balance ensues:

The condensed water effects a calorie influx of about 10,500 kilojoules (2,500 calories). Approximately, a specific heat of 0.84 kilojoules (0.2 calories) per kilogram can be ascribed to the process material.

Since the 85 kg of fed process material requires only 71.2 kilojoules (17 calories) to be heated up 1° C., in this operation the temperature of the process material has increased by about 15° C., from 45° C. to 60° C.

By the application of the vacuum or the associated vaporization, this energy is consumed again so that after the moisture removal of the first cycle, the original temperature of the material of 45° C. should be reinstated. Since the shell temperature of the process chamber is however 65° C., after the first cycle a process material temperature of approx. 50° C. ensues, since by the convection of the in flowing water vapor/hot air mixture, the heat transfer at the chamber wall is slightly intensified. With a process material temperature of 50° C., the reaction temperature with calcium carbonate is still negligibly low.

If this cycle is repeated after moisture removal, a process material temperature of about 55° C. will ensue, which in the case of moisture removal with about 10 mbar, suffices to produce a stable, dry end product.

If the cycle is repeated a third time, the stability of the end product becomes even higher, but the effervescent effect is reduced somewhat because about 20% of the originally infed calcium carbonate has been converted, in the intermediate layer, into calcium citrate.

By varying the amount of introduced water vapor, the temperature and the vacuum, the reactivity or the temperature of effervescence of the end product can be controlled as desired.

With the configuration described, the process which is once defined can be controlled e.g. as follows by a program:

The control valve 142, which is controlled e.g. by a pressure valve and which generates a vacuum of e.g. 700 mbar in the process chamber 84, is closed at the selected time of the program such that pump 16 brings the process chamber 84 up to full vacuum.

If the valve 142 is opened again, with a corresponding adjustment, an amount of e.g. 500 ml water is fed into the process chamber 84 within a selected time unit of e.g. 2 min. When this time has elapsed valve 142 is closed and e.g. after a further 60 seconds, valve 152 is opened to reach full vacuum. When the vacuum in the process chamber has reached an end value of e.g. 20 mbar, the cycle can be repeated.

After two or three cycles, the process chamber can be held for about 15 minutes at values of below 10 mbar for the concluding drying of the process material, whereby the reactively formed calcium citrate is also dehydrated, which has a stabilizing effect on the product.

EXAMPLE 8

Crystallized citric acid of crystal size 0.3 to 0.6 mm totaling 33 kg, 10 kg of pulverized citric acid, 5 kg of micronized calcium carbonate, 3 kg sodium fluorophosphate and 200 g of food coloring are introduced into reaction chamber (14) and heated therein to 45° C.

Under the conditions of example 7, the cycle is now run through a total of three times. After subsequent drying, the coloring substance as well as the sodium fluorophosphate is distributed uniformly by the high solubility of the sodium fluorophosphate under the action of the condensing vapor. When the individual particles are examined under the microscope, as well as in analysis, significant differences in the distribution cannot be established.

EXAMPLE 9

In a vacuum mixing drum, 90 parts of raw sugar and 10 parts of vitamin C are brought up to about 40° C. A constant vacuum of 600-900 mbar is then applied. Then a flow of 1 part water to 20 parts air is allowed to pass through the mixture, agitation being done three dimensionally (oscillating) at a high agitation rate. The process takes about 60 seconds. The air supply valve is then closed and the low constant vacuum is replaced via a valve control by the full pump delivery with the drying process taking about 60 seconds. After these 60 seconds, an end value of about 30 mbar is reached.

At this moment, the air-water vapor valve is opened, thereby effecting the change over to the previous constant vacuum. These steps can be repeated 5 to 10 times, requiring a maximum time of 30 minutes. The resultant granulate is absolutely uniform. Even added coloring substances would be distributed absolutely uniformly, and the product can be discharged via a rotating screen completely dust-free for further processing or packing.

EXAMPLE 10

Ninety five parts of lactose are mixed with 4.5 parts of polyvinyl pyrrolidone and 0.5 part of a highly active hormone and heated to 40° C. A constant vacuum of about 800 mbar is then applied.

In this case a solution of acetone in air as an agglomeration agent is blown into a solution. This solution can consist of 1 part of acetone in 5 to 10 parts of air.

If in the case of, e.g. lactose, of a grain size of 0.2 mm is used, after treatment of 5 steps, total anchorage of the hormone with the lactose results. Even when the most exacting methods of analysis are used, difference in the distribution cannot be established.

However, the process becomes especially interesting when materials are processed which are dispersible only with difficulties, such as e.g. colloids or pseudocollides, polymetacryl acid ester, shellac, waxes and the like.

If injection of the air-solvent mixture is repeated in several steps, eventually 20 or even 30, any desired type of delayed release of the active substances can be achieved in the simplest conceivable form and using easy-to-use automation measures.

EXAMPLE 11

A powder mixture weighing 200 g and, consisting of 150 kg naproxen, 22 kg filler, 20 kg water and 8 kg polyvinyl pyrrolidone, are placed in a vacuum drum with a volume of 720 liters and a useful capacity of 300 liters.

First, the vacuum valve is opened and a vacuum of 200 mbar is produced for about 50 seconds. The vacuum valve is then closed and hot air of 130° to 140° C. is forced in for 30 to 120 seconds from the hot air generator until the pressure in the treatment drum is about 1 bar. Vacuum is then reapplied for 50 seconds and the treatment is cyclically repeated. During the hot air pressure phase, the moisture migrates from inside the grains to the outside, and the moisture already on the outside is given off to the hot air. A certain amount of convection also occurs. During the vacuum phase, the air laden with vapor is extracted. Within 20 minutes the entire powder charge is dried to a residual wetness of 0.1 to 0.2%.

EXAMPLE 12

Fifty kilograms of crystallized citric acid having a grain size 0.3 to 0.6 mm, 15 kg magnesium oxide powder and 15 kg pulverized citric acid are introduced in the reaction vessel and heated to 50° C. A constant vacuum of 700 mbar is generated and during 2 minutes an air/vapor mixture (1 part by volume water vapor in 20 parts by volume air) is introduced under a pressure of 1.5 bar and passed through the mixture that is actuated in three dimensions with 10 rotations per minute. Afterwards, the air inlet is closed and the mixture dried for 2 minutes to a vacuum of 20 mbar. Thereby, the magnesium oxide, assisted by the powdered citric acid is anchored at the surface of the citric acid crystals under the formation of a magnesium citrate binding layer. This procedure is cyclically repeated four times. In the fourth cycle, 15 kg of anhydrous potassium carbonate (70% smaller than 0.2 mm) are added which now reacts with the still free surface of citric acid, at least partially and is anchored there Final drying is carried out with two rotations per minute to a vacuum of 10 mbar, and natural aromatic substances, artificial sweeteners and eventually fillers are added.

EXAMPLE 13

Forty kilograms of citric acid (grain size 0.4 to 0.6 mm), 2.4 kg sweetener and 18 kg iron-2-gluconate are entered into a vacuum granulator having a wall temperature of 65° C. The mixture is heated up to 50° C. A constant vacuum of 600 mbar is applied. The air heating device is adjusted to 120° C. The pumps 11, 16 and the valves are controlled in such a way that 500 pulses per minute of hot air enter the process chamber. During 2 minutes, an amount of 400 ml water are introduced into the air heater and evaporated. The resulting air-vapor mixture condenses on the particles and anchors the iron gluconate powder on the citric acid crystals while forming an agglomerate.

After the introduction of the water, full vacuum is applied and the mixture dried under intermittent agitation to 20 mbar. This procedure removes the water in about 5 minutes. Finally, 10 kg sodium hydrocarbonate are added and the cycle is repeated whereby a partial surface reaction between the citric acid and the sodium hydrocarbonate occurs.

After drying again to 20 mbar, a second 10 kg sodium hydrocarbonate are added, and the cycle is repeated. The product is now finally dried down to 20 mbar at a temperature of 50° C. Three kilograms of an aroma and 4 kg fillers are added. The granulate is discharged via a screen.

Although the present invention has been described in connection with a plurality of preferred embodiments thereof, many other variations and modifications will now become apparent to those skilled in the art. It is preferred, therefore, that the present invention not be limited by the specific disclosure herein, but only by the appended claims.

What is claimed is:

1. In a process for heat treating agitated powder or granulate material contained in a closed drum wherein hot gas is driven through the material, the improvement which comprises the gas comprising a treatment agent and a carrier gas at a temperature sufficient that the treatment agent is present in the vapor state and is drawn through the agitated material, said material being at a temperature below the boiling temperature of the treatment agent and at nearly pressure, and after the desired reaction time, the treatment agent condensed on the material is evaporated and drawn out of the drum by the application of a vacuum at or below the pressure corresponding the boiling point of the treatment agent.

2. The process of claim 1, for the partial dehydration of material containing water of crystallization, wherein the treatment agent is an alcohol.

3. The process of claim 1, wherein at least during a part of the process a vacuum of about 600 to about 900 mbar, prevails in the drum.

4. The process of claim 1, wherein the gas flow is directed through the material being treated via at least one pipe to impinge finely distributed on a large number of points of the material.

5. The process of claim 4, wherein at least during a part of the process a vacuum of about 600 to about 900 mbar, is maintained in the drum.

6. The process of claim 4, for the partial dehydration of a material and containing water of crystallization, wherein the treatment agent is an alcohol.

7. A process for the treatment of material in a closed drum, wherein intermittently, until a predetermine result is achieved
   (i) a hot gas flow is passed over or through a charge of solid, granulate material, and
   (ii) wherein hot air in the drum is extracted by vacuum, characterized in that the hot gas flow before entering the drum is under pressure and contains vaporous treatment agent, and wherein the drum wall is heated and wherein the hot gas supply is interrupted during at least a part of the extraction phase.

8. The process of claim 7, wherein the hot gas is of such a temperature and contains a vapor content so that the vapor does not condense on the material.

9. The process of claim 8, wherein measured at a time during the extraction, the pressure difference between the entry and the exit of the hot gas is not greater than 0.4 bar.

10. The process of claim 7, wherein the pressure differential between the entry and the exit of the hot gas is a minimum of 600 mbar.

11. The process of claim 7, wherein the material is agitated every 60 to 300 seconds.

12. The process of claim 7 for the manufacture of a product containing at least one toxicologically acceptable, water-soluble acid in a relatively coarse-grained form as well as at least one relatively fine-grained reactant wherein the water is used as treatment agent and is introduced in a quantity which is just sufficient to bind the reactant to the surface of the coarse-grained acid.

13. The process of claim 12, wherein the fine-grained reactant is calcium carbonate, and wherein about 1 to 5 volumetric parts of hot air are laden with one volumetric part of water vapor.

14. The process of claim 13 wherein 2 to 4 volumetric parts of hot air are laden with one volumetric part of water vapor.

15. Process as claimed in claim 12, wherein at least one first member of the group consisting of oxides, hydroxides and salts, a second member of the group consisting of alkaline carbonates of hydrocarbonates are fine-grained reactants.

16. A process for heat treating an agitated powder or granulate material comprising passing a hot gas having entrained therein a vaporized treatment agent, the boiling point of the treatment agent being between 0° and 200° C. and the temperature of the hot gas being at least 10° greater than said boiling point and the concentration of said agent being from 0.1 to 55 volume %, through a vacuum vessel containing said powder or granulate at a temperature below the boiling point of said treatment agent, with the prevailing vacuum and temperature conditions being such that at least a part of the treatment agent condenses, thereafter adjusting said prevailing conditions such that at least a part of the condensed treatment agent vaporizes, and removing the vessel vaporized treatment agent from the vessel.

17. The process of claim 16 wherein said sequence of condensation and vaporization is repeated at least once.

18. The process of claim 17 wherein said treatment agent has a boiling point from room temperature to 100° C., said hot gas has a temperature from 110° to 150° C. which is at least 20° greater than said boiling point, and the vacuum in said vessel during the condensation treatment is 200 to 400 mbar and is 10 to 30 mbar during the vaporization.

* * * * *